US00PP31424P2

(12) United States Plant Patent
Hansen

(10) Patent No.: US PP31,424 P2
(45) Date of Patent: Jan. 28, 2020

(54) ***KNIPHOFIA* PLANT NAMED 'BACKDRAFT'**

(50) Latin Name: *Kniphofia hybrida*
Varietal Denomination: Backdraft

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 36 days.

(21) Appl. No.: 16/350,527

(22) Filed: Nov. 28, 2018

(51) Int. Cl.
*A01H 5/02* (2018.01)

(52) U.S. Cl.
USPC ..... Plt./443

(58) Field of Classification Search
USPC ..... Plt./443
CPC ..... A01H 5/02
See application file for complete search history.

*Primary Examiner* — Annette H Para

(57) ABSTRACT

A new and distinct cultivar of Red Hot Poker plant named *Kniphofia* 'Backdraft' with long, gracefully-arching, strap-like, keeled, glaucous, gray-green foliage and numerous scapes beginning in early summer and repeating though early fall. Habit is densely growing, winter-hardy and tolerant of heat. Numerous scapes of intense reddish-orange flowers that mature to pale yellow on short scapes beginning in early summer and repeating into early October. The new plant is useful for landscaping as a specimen, en masse, or as a long-lasting cut flower.

1 Drawing Sheet

Botanical classification: *Kniphofia hybrida.*
Variety denomination: 'Backdraft'.

STATEMENT REGARDING PRIOR DISCLOSURES UNDER 37 CFR 1.77(B)(6)

The first public disclosure of the claimed plant, in the form of a sale, was made by Walters Gardens, Inc. on Sep. 24, 2018. Prior to that, on Dec. 1, 2017 the claimed plant was displayed with a photograph and brief sales promotion on the website of Walters Gardens, Inc., who obtained the plant and all information relating thereto, from the inventor. No plants of *Kniphofia* 'Backdraft' have been sold, in this country or anywhere in the world, nor has any disclosure of the new plant been made, more than one year prior the filing date of this application, and such sale or disclosure within one year was either derived directly or indirectly from the inventor.

BACKGROUND AND ORIGIN OF THE PLANT

The present invention relates to the new and distinct Red Hot Poker, *Kniphofia* 'Backdraft' developed under the direction of the inventor at a wholesale perennial nursery in Zeeland, Mich., USA in the summer of 2012. The new plant was the result of a single seedling selection from a cross of 'Echo Rojo' U.S. Plant Pat. No. 22,791 as the female or seed parent and 'Papaya Popsicle' U.S. Plant Pat. No. 22,915 as the male or pollen parent in 2012. The plant passed initial evaluation in the summer of 2014 and was subsequently given the breeder code KNIP-12-402-12 prior to naming. *Kniphofia* 'Backdraft' has been successfully asexually propagated by division method since 2014 at the same wholesale perennial nursery in Zeeland, Mich. and subsequently by shoot tip tissue culture, and both methods have been found to be stable and produce identical plants that maintain the unique characteristics of the original plant through successive generations.

SUMMARY OF THE PLANT

*Kniphofia* 'Backdraft' differs from its parents as well as all other *Kniphofia* known to the applicant. The most similar known *Kniphofia* cultivars are the female parent 'Echo Rojo', 'Mango Popsicle' U.S. Plant Pat. No. 22,968, the male parent 'Papaya Popsicle', 'Poco Orange' U.S. Plant Pat. No. 27,677 and the co-pending application 'Poker Face' U.S. Plant Pat. No. 30,346. 'Echo Rojo' has flowers that are more spaced on the peduncle. 'Mango Popsicle' is much shorter in scape and foliage height with more yellow-orange flower coloration. 'Papaya Popsicle' is shorter in scape and foliage height with slightly more reddish orange flower color. 'Poco Orange' is smaller inscape height, foliage height and overall habit and has a lighter orange flower color with less red hue. 'Poker Face' is a sibling of 'Backdraft' with taller flower scapes and foliage height.

*Kniphofia* 'Backdraft' differs from these above cultivars and all cultivars known to the inventor in that it has:

1. Gracefully arching, strap-like, keeled, gray-green foliage.
2. Rapidly growing, dense habit, winter-hardy, heat tolerant, moderate-sized clumps.
3. Numerous spikes of intense reddish-orange flowers that mature to pale yellow on short stems;
4. Flowering beginning the first week of summer and repeating into early October in Michigan.

BRIEF DESCRIPTION OF THE DRAWINGS

The photographs of *Kniphofia* 'Backdraft' demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
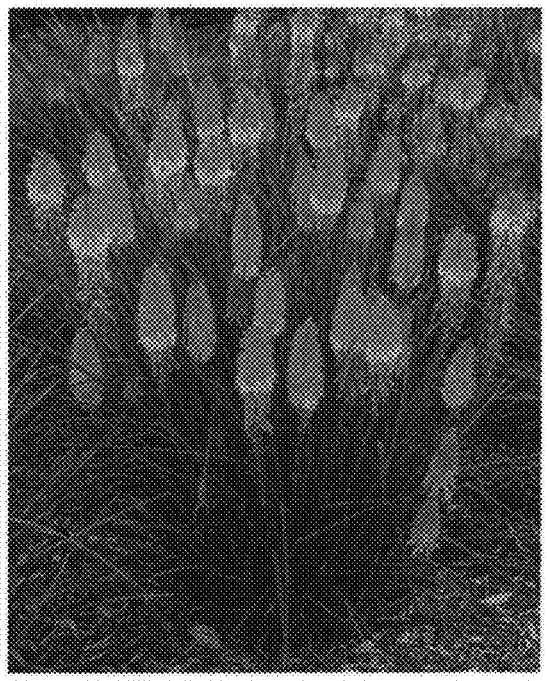
FIG. 1 shows the side-view habit of a six-year-old plant in midseason flowering.
Figure 2:
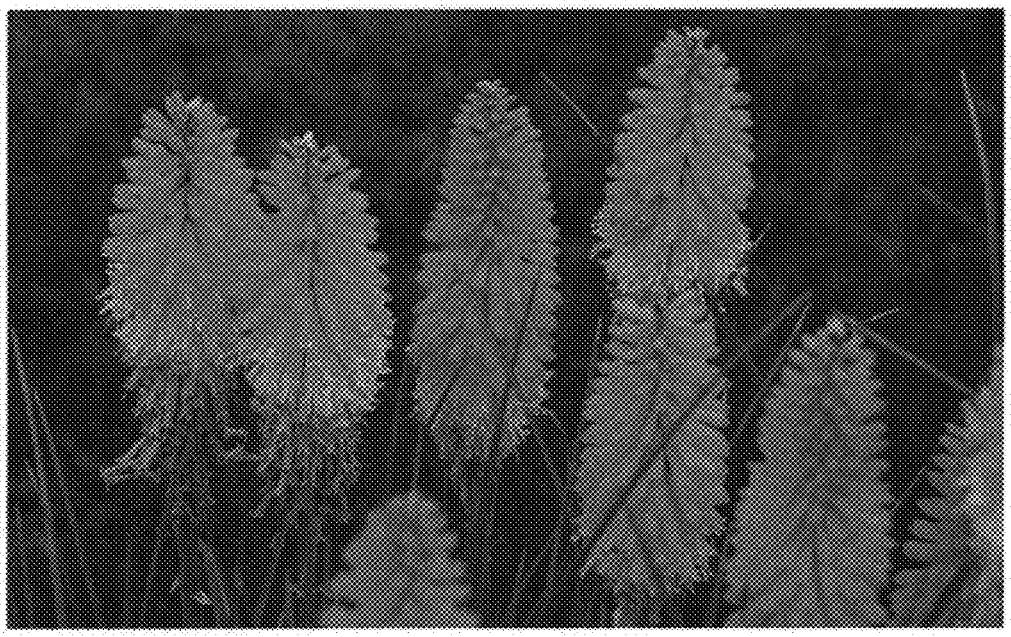
FIG. 2 shows a close-up of the flowers and buds.

The following descriptions and color references are based on the 2015 edition of The Royal Horticultural Society Colour Chart except where common dictionary terms are used. The new plant, *Kniphofia* 'Backdraft', has not been observed under all possible environments. The phenotype may vary slightly with different environmental conditions, such as temperature, light, fertility, moisture and maturity levels, but without any change in the genotype. The following observations and size descriptions are of a six-year-old plant in a trial garden of a wholesale perennial nursery in Zeeland, Mich. under full sun with supplemental water and fertilizer as needed.

Botanical classification: *Kniphofia* hybrid;

Parentage: *Kniphofia* 'Echo Rojo' as the female or seed parent and 'Papaya Popsicle' as the male or pollen parent;

Propagation method: By garden division of the rhizome and shoot tip tissue culture;

Growth rate: Vigorous, flowering in 3.5 liter containers in about 10 to 12 weeks from a 25 mm plug liner in late winter to spring and from a one-year-old bare root plant to flowering in 6 to 8 weeks in a 4.0 liter container;

Rooting habit: Fibrous from base of rhizomes, lightly branching; color nearest RHS 158C;

Plant description: Dense, rhizomatous, acaulescent, perennial clump with long thin foliage to about 105.0 cm across and about 78.0 cm tall; flowering to about 82.0 cm tall; about 128 peduncles per plant;

Leaves: Linear; keeled at base, triangular in distal half; arranged about 8 leaves per basal division; apex narrowly acute; base truncate, clasping; margin entire; no fragrance observed;

Leaf size: To about 81.0 cm long and 18.0 mm across at base, average about 72.0 cm long and 14.0 mm across at base;

Leaf color: Young base nearest RHS 150D both abaxial and adaxial, distally nearest RHS 144A both abaxial and adaxial; mature adaxial nearest RHS 138A and abaxial between RHS 138A and RHS 146B;

Leaf venation: Parallel; color same as leaf abaxial and adaxial;

Stem: Acaulescent; rhizome about 18.0 mm across at base;

Inflorescence: In spike-like raceme occasionally with single branch to about 12 cm long and 2.0 mm diameter; cylindrical; about 140 flowers per stem; flowering portion to about 24.0 cm tall and about 6.0 cm across; lasting about three weeks; flower spacing less than 1.0 mm apart on raceme in distal region and about 2.5 cm in lowest flowers;

Peduncle: Terete; glabrous; glaucous; solid not fistulose; to about 82.0 cm long and 9.0 mm diameter; average 68.0 cm tall and 8.0 mm diameter;

Peduncle color: Nearest RHS 146B;

Buds one day prior to opening: Ellipsoidal to tubular with swollen subacute apex and rounded base; glabrous; lustrous; about 22.0 mm long and about 2.5 mm diameter at base and 6.0 mm diameter at widest point near apex;

Bud attitude: Beginning outwardly and drooping as maturing toward anthesis;

Bud color: Abaxial distal and dorsal portions nearest RHS N25A becoming nearest RHS 26A in ventral with ventral veins nearest RHS N25A;

Flowers: Cylindrical forming tubular corolla; perfect; actinomorphic; individually open and effective about three to four days;

Flower size: To about 24.0 mm long, fused in basal about 21.0 mm; face to about 9.0 mm tall and about 9.0 mm wide; corolla tube to about 21.0 mm long, 3.5 mm diameter near base and about 5.5 mm diameter near throat;

Flower attitude: Drooping;

Flower fragrance: None detected;

Flowering period: Individual racemes effective for about 3 weeks; beginning early summer Michigan for about six week, then continuing with repeat racemes until early fall with a short two week break in the heat of the summer;

Tepals: Six, in two sets of three; both sets with acute apices and fused in basal 21.0 mm forming tube; margin entire; glabrous and lustrous abaxial and adaxial; about 24.0 mm long and about 3.0 mm across just above fusion point; inner set with lighter 1.0 mm wide margin;

Tepal color (young abaxial): Distal one-third of both sets nearest RHS 26B; basal two thirds nearest RHS 24B; inner set with 1.0 mm margin of RHS 11D; both sets with midrib nearest RHS N25A in distal one-half and basal midrib becoming nearest RHS 24B; (young adaxial): dorsal tepals distal region nearest RHS 24B with midrib of nearest RHS N25B; ventral tepals nearest 23D with distal midrib nearest RHS 23C; inner set with 1.0 mm margin nearest RHS NN155;

Tepal color (mature abaxial): Both inner and outer sets identical with midribs nearest RHS 12C and remainder nearest RHS 11C; (mature adaxial): inner and outer sets identical nearest RHS 11D;

Androecium: Six; variable lengths;

*Filaments*.—Six; exserted; cylindrical; glabrous; lustrous; from about 31.0 to 37.0 mm long and about 0.7 mm diameter; color nearest RHS 1D.

*Anther*.—Slightly flattened ellipsoidal; flattened ventrally to dorsally; about 2.0 mm long and 1.5 mm across and 1.0 mm thick; color nearest RHS 14A.

*Pollen*.—Abundant: color nearest RHS 10A.

Gynoecium: Single; about 30.0 mm long;

*Style*.—Cylindrical; glabrous; lustrous; about 28.0 mm long and 0.3 mm diameter: color nearest RHS 1C except the distal 1.0 m nearest RHS 20A.

*Stigma*.—Flattened, round; about 0.3 mm across; color nearest RHS 158D.

*Ovary*.—Superior; globose; rounded apex, truncate base; about 2.5 mm long and 2.5 mm diameter; color nearest RHS 144C.

Pedicel: Terete; glabrous; stiff; drooping with maturity; about 2.0 mm long and about 1.0 mm diameter;

Pedicel color: Nearest RHS 174D;

Bracts: Lanceolate; at cauline nodes and subtending individual flowers; with acute apices and truncate base; to about 6.0 mm long and 4.0 mm across at base; decreasing distally; average about 5.0 mm long and 2.5 mm across; color nearest RHS 164D;

Fruit: Tri-valved loculicidal capsule; ellipsoidal; about 6.0 mm long and 5.0 mm across; glabrous; with rounded apex and rounded base; typically four to nine seeded; color upon maturity nearest RHS 200A;

Seed: Irregular with angular sides, acute apex and base; about 4.0 mm and 2.5 mm across; color nearest RHS 200A;

Disease and pest resistance: 'Backdraft' resistance beyond that of other *Kniphofia* has not been observed. The plant grows best with good drainage and is able to tolerate some heat when established. Hardiness at least from USDA zone 6 through 9 and 5b with protection.

I claim:

1. A new and distinct cultivar of *Kniphofia* plant named 'Backdraft' as herein described and illustrated.

* * * * *